(12) United States Patent
Pernu et al.

(10) Patent No.: US 9,861,291 B2
(45) Date of Patent: Jan. 9, 2018

(54) ELECTRODE ASSEMBLY

(71) Applicant: SUUNTO OY, Vantaa (FI)

(72) Inventors: Kimmo Pernu, Vantaa (FI); Tapio Selby, Vantaa (FI)

(73) Assignee: Suunto Oy, Vantaa (FI)

( * ) Notice: Subject to any disclaimer, the term of this patent is extended or adjusted under 35 U.S.C. 154(b) by 855 days.

(21) Appl. No.: 14/144,627

(22) Filed: Dec. 31, 2013

(65) Prior Publication Data

US 2014/0187899 A1  Jul. 3, 2014

Related U.S. Application Data

(63) Continuation-in-part of application No. 13/832,598, filed on Mar. 15, 2013, now Pat. No. 9,597,005.

(60) Provisional application No. 61/747,386, filed on Dec. 31, 2012.

(30) Foreign Application Priority Data

Dec. 31, 2012  (FI) ...................................... 20126396
Jan. 29, 2013  (GB) .................................... 1301566.4

(51) Int. Cl.
    *A61B 5/04* (2006.01)
    *A61B 5/0416* (2006.01)
    *A61B 5/00* (2006.01)
    *A61B 5/0408* (2006.01)

(52) U.S. Cl.
CPC .......... *A61B 5/0416* (2013.01); *A61B 5/0006* (2013.01); *A61B 5/6804* (2013.01); *A61B 5/04085* (2013.01); *A61B 5/6831* (2013.01); *A61B 2562/227* (2013.01)

(58) Field of Classification Search
CPC ... A61B 5/0416; A61B 5/6804–5/6806; A61B 2562/227; A61B 5/0408; A61B 2560/0462; A61B 2560/0468; A61B 2562/22; A61B 2562/225; Y10T 24/45984
USPC .......... 600/394, 388–390; 439/909, 282, 818
See application file for complete search history.

(56) References Cited

U.S. PATENT DOCUMENTS

| 17,340,448 | | 11/1929 | Reiter |
| 2,688,785 | A | 9/1954 | Carpinella |
| 3,750,094 | A | 7/1973 | Zenkich |
| 3,882,853 | A * | 5/1975 | Gofman ............... A61B 5/0416 600/391 |

(Continued)

FOREIGN PATENT DOCUMENTS

| CN | 1078131 A | 11/1993 |
| CN | 1090153 A | 8/1994 |

(Continued)

*Primary Examiner* — Lee S Cohen
*Assistant Examiner* — Erin M Cardinal
(74) *Attorney, Agent, or Firm* — Seppo Laine Oy

(57) ABSTRACT

The present invention relates generally to an electrode assembly including a thin, low thickness snap for use, for example, in a heart rate monitoring. The electrode assembly can come in the form of a kit with multiple pieces or in an assembled form. The electrode assembly includes two electrodes with respective snaps connected by a non-stretchable material portion. The electrode assembly can be easily integrated into a garment with minimal interference in the usability of the garment itself. Additionally, the present invention relates to a garment having integrated therein an electrode assembly.

17 Claims, 10 Drawing Sheets

(56) References Cited

U.S. PATENT DOCUMENTS

| | | | |
|---|---|---|---|
| 4,490,005 A | | 12/1984 | Hovey |
| 4,706,344 A | * | 11/1987 | Tanaka ..................... A44B 1/44 24/114.4 |
| 4,996,989 A | * | 3/1991 | Stundel ................ A61B 5/0478 600/383 |
| 5,435,043 A | * | 7/1995 | Ito .......................... A41H 37/04 24/114.4 |
| 5,645,063 A | | 7/1997 | Straka, Jr. |
| 6,067,694 A | | 5/2000 | Candotti |
| 2004/0138546 A1 | * | 7/2004 | Reho .................. A61B 5/04085 600/382 |
| 2006/0211934 A1 | | 9/2006 | Hassonjee et al. |
| 2007/0184682 A1 | * | 8/2007 | Gobron .............. A61B 5/04085 439/67 |
| 2007/0285868 A1 | | 12/2007 | Lindberg et al. |
| 2009/0043185 A1 | * | 2/2009 | McAdams ......... A61B 5/04087 600/372 |
| 2009/0292192 A1 | * | 11/2009 | Silber ................ A61B 5/04085 600/372 |
| 2010/0191090 A1 | * | 7/2010 | Shin ..................... A61B 5/6831 600/388 |
| 2011/0016679 A1 | * | 1/2011 | Candotti ............ A44B 17/0011 24/700 |
| 2012/0165645 A1 | | 6/2012 | Russell et al. |
| 2013/0338472 A1 | * | 12/2013 | Macia Barber .... A61B 5/04085 600/388 |
| 2014/0296651 A1 | * | 10/2014 | Stone ................... A61B 5/6804 600/301 |
| 2015/0157265 A1 | * | 6/2015 | Kang .................. A61B 5/6831 600/394 |

FOREIGN PATENT DOCUMENTS

| | | |
|---|---|---|
| CN | 2496395 Y | 6/2002 |
| CN | 101084826 A | 12/2007 |
| CN | 101945593 A | 1/2011 |
| EP | 0390400 A1 | 10/1990 |
| EP | 1541190 A1 | 6/2005 |
| EP | 2368940 A1 | 9/2011 |
| GB | 755563 A | 8/1956 |
| WO | WO 02071935 A1 | 9/2002 |
| WO | WO 2004002311 A1 | 1/2004 |
| WO | WO 2005032365 A1 | 4/2005 |
| WO | WO 2005032366 A1 | 4/2005 |
| WO | WO2006079888 A1 | 8/2006 |
| WO | WO2008133394 A1 | 11/2008 |
| WO | WO2011131233 A1 | 10/2011 |
| WO | WO2014102459 A1 | 7/2014 |

* cited by examiner

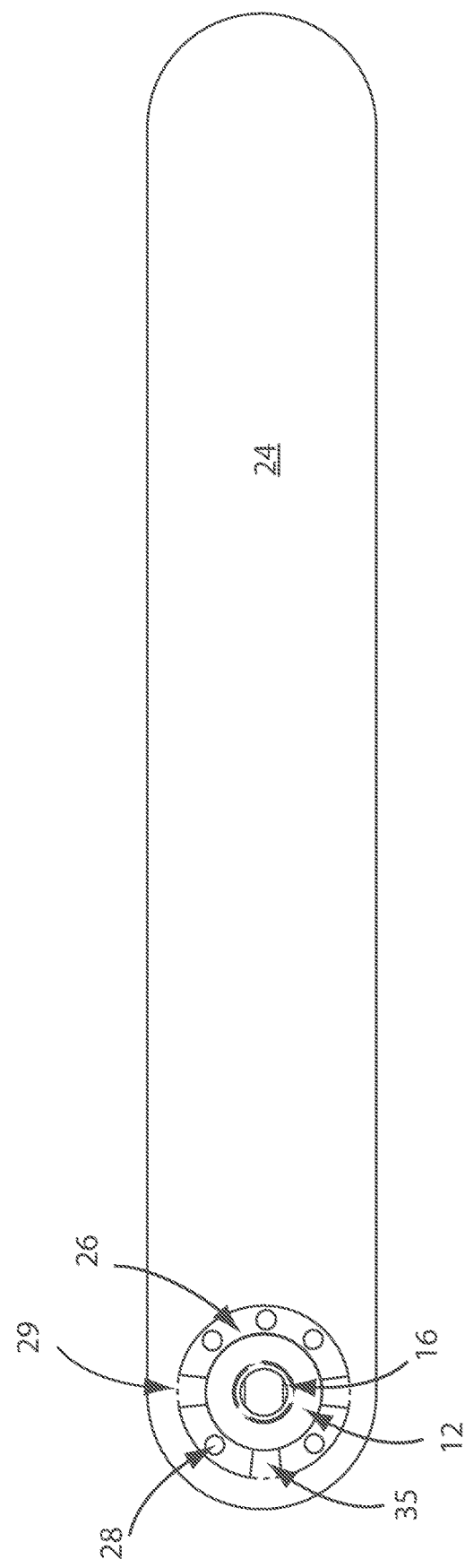

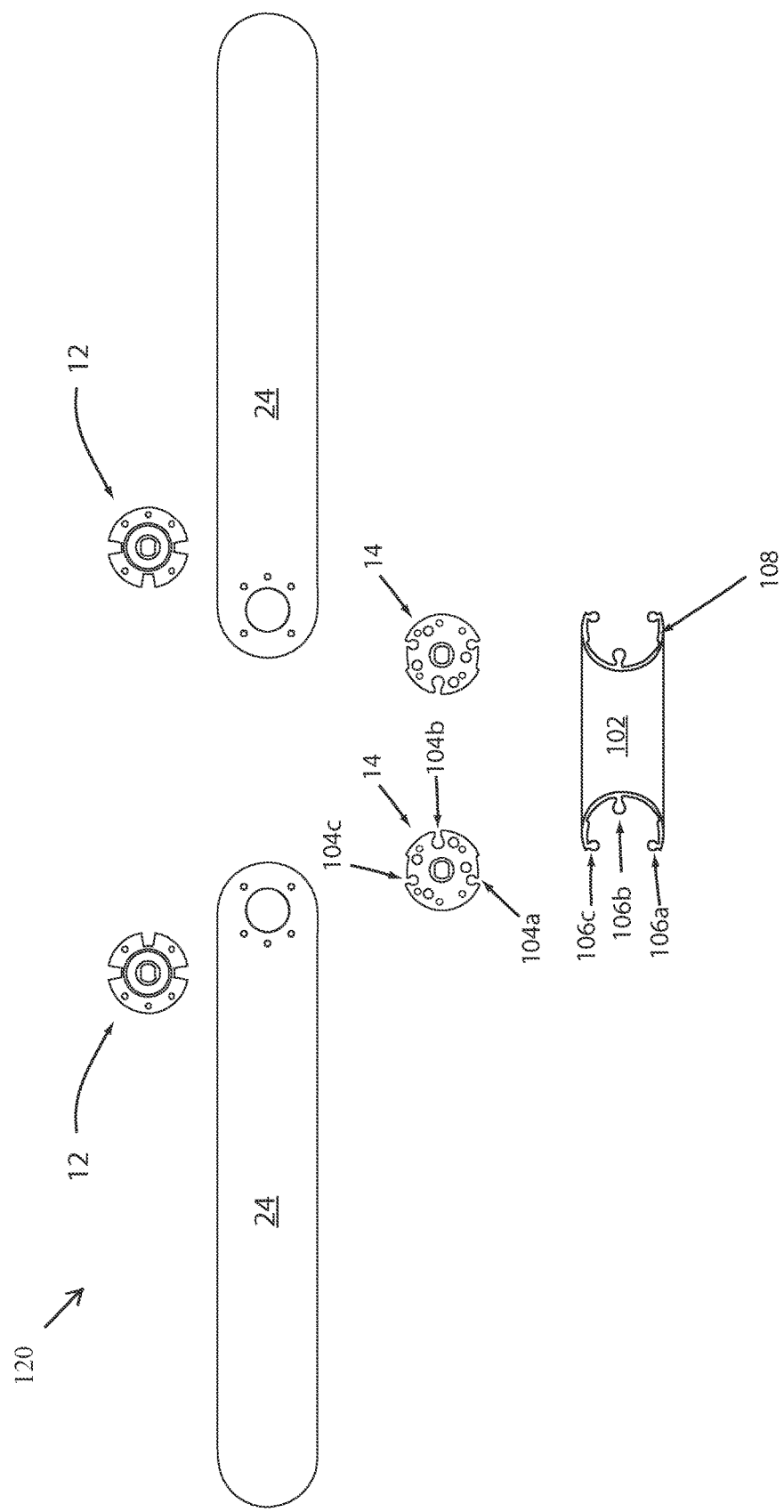

ELECTRODE ASSEMBLY

This application is a continuation in part of Application No. 13/832,598, filed Mar. 15, 2013, now U.S. Pat. No. 9,597,005.

FIELD OF INVENTION

The present invention relates generally to an electrode assembly having at least two snap portions. More particularly, embodiments of the present electrode assembly are particularly well suited for receiving, holding and enabling an electrical connection with male ends of a telemetric device. Examples of the present electrode assemblies are integrated within a heart rate monitor belt or garment.

BACKGROUND OF THE INVENTION

Currently, there are heart rate monitor belts which people can wear underneath their clothing in order to monitor their heart rate. Such belts are typically designed such that a telemetric transmitter is detachably connected to a belt having two electrodes which are in contact with the user's skin in the chest region of the user's torso. The electrodes identify an electric ECG pulse caused by the heart and then the detachable telemetric transmitter transmits data indicative of the user's heart beat with the use of wireless magnetic near field communication or a radio signal to a remote receiver provided with a display. In many instances the remote receiver is provided in the form of a wrist watch, wrist top computer or other similar display carried by a user, typically on the user's wrist.

Since various acceleration and magnetic sensors can be integrated in small and lightweight devices, the telemetric data to be transferred may, instead of or in addition to the heart rate, comprise a plurality of measured variable data, such as working frequency, pedaling rate and pedaling frequency, travel speed, etc. The data to be transferred may additionally comprise data required for the identification of the user and/or the transmitter device.

U.S. application Ser. No. 11/808,391 filed Jun. 8, 2007 and published as US 2007/0285868 which is herein incorporated by reference in its entirety, for instance, discloses a heart rate monitor belt which comprises a plurality of electrodes and a detachable telemetric transmitter.

It is preferably to have a telemetric transmitter which is detachable from a heart rate monitor belt for several reasons. From a consumer point of view, a user is typically sweating while using a heart rate monitor belt and it is therefore advantageous to be able to separate the electronic telemetric transmitter from the belt so that the belt can be washed. From a manufacturing point of view, the process for manufacturing the belt is substantially different from that of manufacturing the transceiver and therefore it is beneficial to be able to manufacture the components separately. Additionally, it is beneficial for one telemetric transmitter to be interchangeable with a plurality of belts.

Though there are several alternative methods for detachably connecting a telemetric transmitter to a heart rate monitor belt, the industry has almost entirely adopted the use of a pair of standard garment snaps. These standard garment snaps typically are mounted on the material of a heart rate monitor belt and virtually their entire thickness of around 4 mm protrudes from the outer surface of the belt.

Due to the existing technology and methods for detachably connecting telemetric transmitters it has not been realistic to incorporate heart rate monitor electrodes in to typical garments. In fact, the primary road block to such incorporation has been the size and bulkiness of the standard garment snaps. No clothing manufacture, nor consumer, has wanted 4 mm protrusions from their garments such as tops, shirts and sports bras.

Therefore, the garment industry has incurred a long felt need for an improved method of detachably connecting a telemetric transmitter to an article of clothing which does not compromise the integrity and utility of the underlying garment. However, the telemetric transmitter manufacturing industry has already adopted certain standards which relate to the use of a pair of male studs on a telemetric transmitter to be detachably snapped in to a pair of snaps on a heart rate monitor belt. As such, it would not be economical to wholly redesign the male portions of telemetric transmitters and the method in which they connect to an object having the necessary electrodes for measuring a user's heart rate.

Thus, there exists a need for a snap which fulfils the requirements of the garment industry but which fits in at least partially with the existing standards of the telemetric transmitter manufacturing industry. However, several critical issues arise when attempting to merely minimize the existing standardized snap. The main issue is the integrity of the connection between the male stud and the snap. Any amount over movement of the male stud within the snap will create electrical noise which makes difficult to impossible to accurately measure parameters such as a user's heart beat. Additionally, as a user is typically involved in strenuous activity while utilizing the product, the connection needs to withstand, and support the telemetric transmitter during such activity. As the depth of the snap decreases, the forces required to insure a reliably stable connection significantly increase.

Further yet, users typically sweat while undergoing strenuous activity wearing the product. As a reliable electrical connection is necessary between the telemetric transmitter and the electrode on the user's skin, it is important to keep the connection moisture free to reduce the likelihood of any shorts. Similarly, the problem is compounded for users who wish to utilize a heart rate monitor under water, for example while swimming or diving.

Therefore, there exist numerous challenges in the art to the development of a means of detachably connecting a telemetric transmitter to a garment having electrodes for monitoring a user's heart beat which aims to satisfy user's need, the garment manufacturer's needs and the needs of telemetric transmitter manufactures.

SUMMARY OF THE INVENTION

It is an object of the present invention to provide an electrode assembly.

Electrode assemblies according to the present invention are particularly useful as being integrated in to garments. Electrode assemblies described herein may come in a kit form with a plurality of pieces or in a single, assembled form.

According to certain embodiments, an electrode assembly includes a first electrode having an upper cap portion of a snap on one side, a second electrode having an upper cap portion of a snap on one side, and a linking member having a first base portion of a snap and a second base portion of a snap separated by a non-stretchable material portion, wherein the first electrode and the second electrode are coupleable to their respective first and second base portions of the linking member.

The upper cap portion and base portions form a snap. Snaps according to aspects of certain embodiments of the present invention are extremely thin compared to traditional snaps used with electrodes, for example in typical heart rate monitor belts. The thin size of the snaps lend themselves well to integration into garments so that when the snap is not connected, for example to a telemetric device, e.g. a heart rate monitor device and/or an EMG muscle measurement device, the snaps do not impact the wearability of the garment itself.

It is another object of the present invention to provide a garment with at least one electrode assembly integrated therewith.

Still yet, it is a further object of the present invention to provide a linking member which has at least two portions which form base portions for snaps and which have a higher degree of rigidity compared to a non-stretchable material portion connecting said at least two base portions. The linking member of the present invention allows for easy and reliable integration of multiple electrodes and snaps in to a garment with consistent spacing between the snaps. Additionally, the flexible nature of the non-stretchable material portion according to certain embodiments increases the wearability of a garment having one or more of the electrode assemblies.

BRIEF DESCRIPTION OF THE DRAWINGS

FIG. 8 shows an electrode snap assembly in accordance with an embodiment of the present invention.

FIG. 9 shows an electrode assembly 120 in a kit embodiment.

DETAILED DESCRIPTION OF EXEMPLARY EMBODIMENTS

Figure 1:
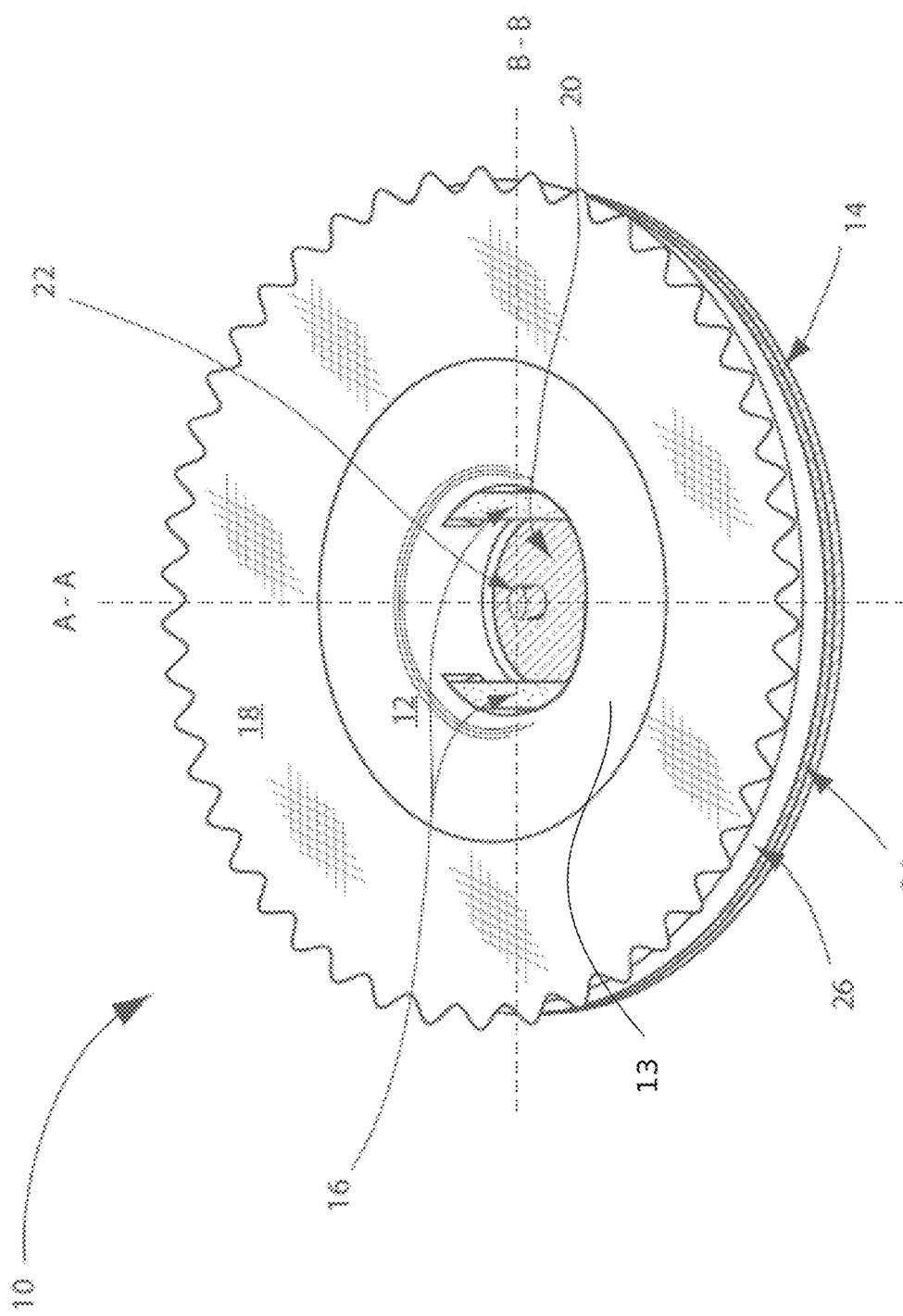
FIG. 1 shows a top perspective view of a snap integrated within a garment in accordance with an embodiment of the present invention.

A snap 10 in accordance with an embodiment of the present invention is shown in FIG. 1. The snap is shown integrated within a material 18. As can be seen from the figure, the upper cap portion 12 of the snap 10 is essentially flush with the material 18, i.e. there is no significant protrusion. Such an integrated snap design is highly desirable when transitioning from stand alone heart rate monitor belts worn in addition to regular clothing to integrating the functionality of a heart rate monitor in to clothing itself.

As discussed herein, a heart rate monitor belt is the combination of electrodes and snaps in such an arrangement that they can be used to determine, measure and/or monitor the heart beat of an individual or animal wearing the belt. A heart rate monitor belt may be a standalone article in the form of, for example, a belt having a plurality of electrodes connected to a pair of snaps which can be worn, for example around the torso of a user. Additionally, a heart rate monitor belt can be integrated within a garment, for example a top or sports bra. As such, a garment having the components necessary for use in monitoring the heart rate of a user similar to a standalone heart rate monitor belt will likewise herein be referred to as a heart rate monitor belt.

A snap 10 in accordance with certain embodiments of the present invention should be integratable within an article. Additionally, the snap 10 should be capable of receiving, holding and enabling an electrical connection with a male end of a telemetric device. A more detailed description of telemetric devices follows below. The snap 10 generally comprises an upper cap portion 12, a base portion 14 and a conductive wire spring 16 as can be seen in FIG. 1.

The upper cap portion 12 includes a recess forming at least a portion of the sides 30 of a socket region 20 of the snap. The socket region 20 is for receiving a male end of a telemetric device. The upper cap portion 12 is more clearly seen in FIG. 2. The upper cap portion 12 has a top portion 13 and recess portion, as seen in FIG. 1, as well as a flange portion 26 as shown more clearly in FIG. 2. The top portion 13 can be generally flat and have a constant width around the recess in the center. In order to integrate in a flush manner with a material, the upper cap portion has a flange 26 which goes out from the top portion 13 at a lower height. In the present example, the top surface of the top portion 13 of the upper cap portion 12 is the top measure of height of the snap.

The amount of depression of the flange 26 compared to the top portion 13 can be equal to or approximately equal to the thickness of material 18 which the snap is to be integrated with. Additionally, the amount of depression can be a standard amount which is selected in order to work best with a wide variety of material thicknesses. However, as can be seen in FIG. 1, it is advantageous for the material 18, being affixed on top of the flange portion 26 of the upper cap portion 12 to be essentially or substantially flush with the top portion 13 of the upper cap portion 12.

The recess in the upper cap portion 12 forms a socket region 20. The sides 30 of the recess generally form the sides of the socket region 20. While the sides 30 of the recess can have a plurality of geometries from generally vertical to something more complex, it is advantageous for the side wall geometry to be complementary to the male end of a telemetric transmitter to be detachable connected to the snap 10. Such geometries will be discussed in more detail below.

Figure 2:
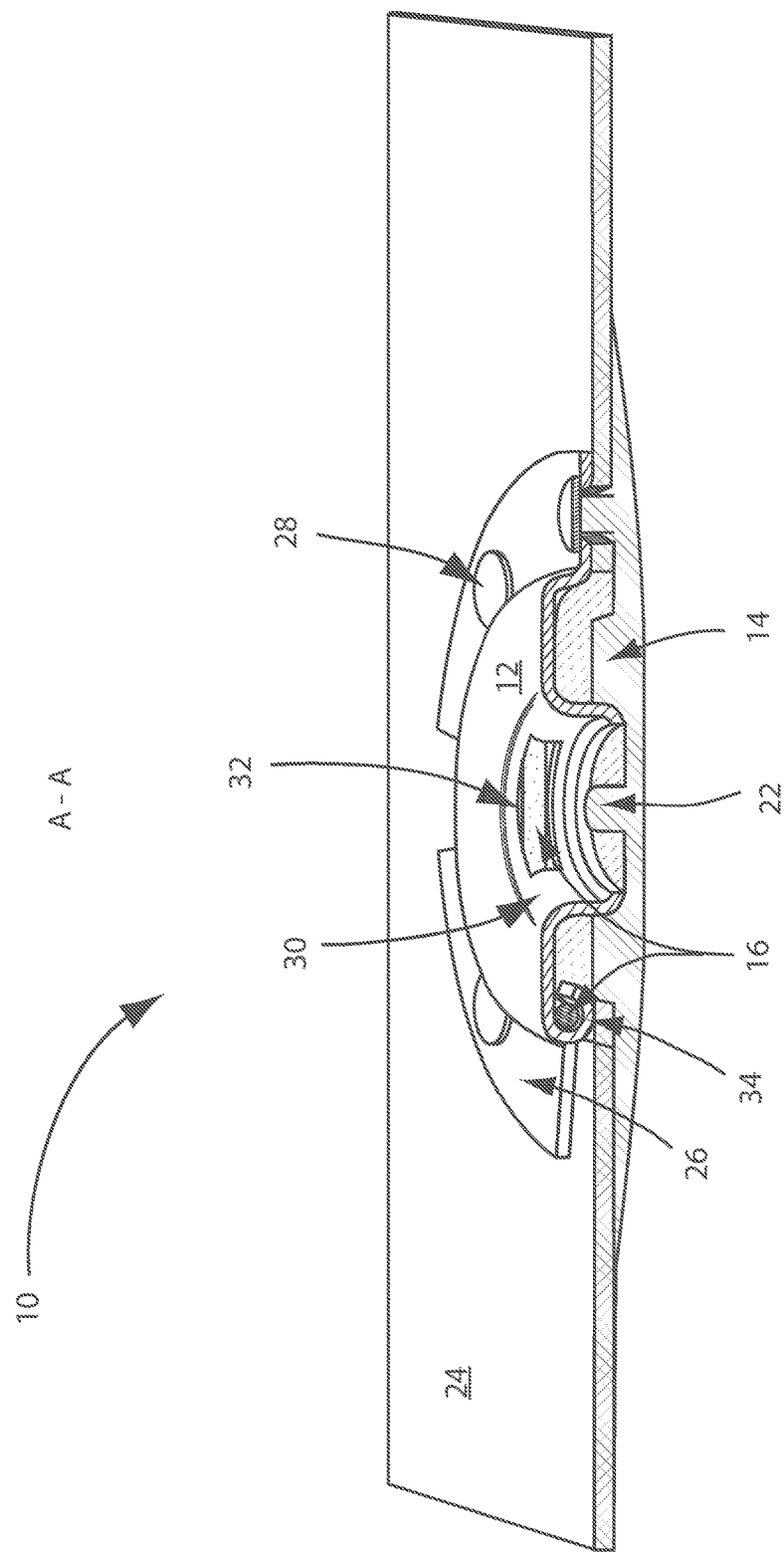
FIG. 2 shows cutaway portion A-A of the integrated snap of FIG. 1 with the material of the garment removed.

The socket region is generally formed by the sides 30 of the recess of the upper cap portion 12 and by a bottom, as seen in FIGS. 1 and 2. In the present examples, the sides 30 of the recess of the upper cap portion 12 extend to the bottom of the socket region 20 and contact a portion of a base portion 14 which forms the bottom of the socket region 20. However, it is possible for a portion of the base portion 14 to extend partially up the sides of the socket region 20 such that the sides of the socket region 20 are formed by a combination of a base portion 14 and the upper cap portion 12. Additionally, the recess of the upper cap portion 12 may comprise the sides and some or all of the bottom portion of the socket region.

In accordance with the present example, the upper cap portion 12 comprises an opening at the bottom of the recess. The upper cap portion 12 is coupled to a separate base portion 14 which forms the bottom of the socket region 20. The upper cap portion 12 and the base portion 14 are coupled in such a manner so that at least the interface at the bottom of the socket region 20 is water tight.

The sides 30 of the recess of the upper cap portion are additionally shown with two openings 32. Openings 32 are arranged at a height in between the top portion 13 and the bottom of the socket region 20 such that a portion of a conductive wire spring 16 can at least partially extend through the opening 32. The conductive wire spring 16 is for releasably holding the male end of a telemetric device within the socket region of the snap. Additionally, the conductive wire spring 16 make, or at least partially makes, the electrical connection between at least one electrode 24 in a garment or heart rate monitor belt and the male end of a telemetric device.

The conductive wire spring 16 is house at least partially within a gap which is formed between the upper cap portion 12 and the base portion 14. More specifically, according to the present example, the gap is formed between the top portion 13 of the upper cap portion 12 and a portion of the base portion 14. The conductive wire spring 16, according to the present example, is mechanically coupled to the upper cap portion 12 by a lip 34 of the upper cap portion 12. The lip 34 may be within the gap formed between the top portion 13 of the upper cap portion 12 and the base portion 14 or the lip 34 may be located in another region of the snap 10. The conductive wire spring 16 may simply rest on the lip 34, there may be a friction fit between the conductive wire spring 16 and the lip 34 and/or other portion of the upper cap portion 12, there may be an additional mechanical means for holding the conductive wire spring 16, there may be a separate, or additional chemical means, such as an adhesive, for holding the conductive wire spring 16 or there may be some combination of the above. According to certain examples, the wire spring 16 is not rigidly affixed to the upper cap portion 12 but is allowed a small degree of movement due to the mechanical fit of the lip 34 arrangement.

According to certain embodiments, as can be seen for example in FIG. 8, the lip 34 which holds the wire spring 16 can be formed from the flange 26 of the upper cap portion 12. One or more notches 35 can be formed, e.g. cut, out from the flange 26 and then bent back towards the socket region 20 to form the lip 34.

An example of conductive wire springs 16 can be a wire springs with a double 'S' shape. The wire spring 16 may have a diameter of between, for example, 0.6 to 0.8 mm. Examples of suitable materials are stainless steels, e.g. AISI 304 or 316. Additionally, the conductive wire spring 16 may be an integral component of either the upper cap portion 12 or the base portion 14.

An example of the conductive wire spring 16 is a double 'S' shape which takes the general shape of a horseshoe. In an example in accordance with FIG. 8, the wire spring 16 can be held by three lips 34 formed from three corresponding notches 35 which hold the wire spring 16 on the three sides of the horseshoe. As a result, two interior legs of the horseshoe, i.e. one leg from each of the 'S''s floats free and extends through the openings 32 in the side of the socket region.

Figure 3:
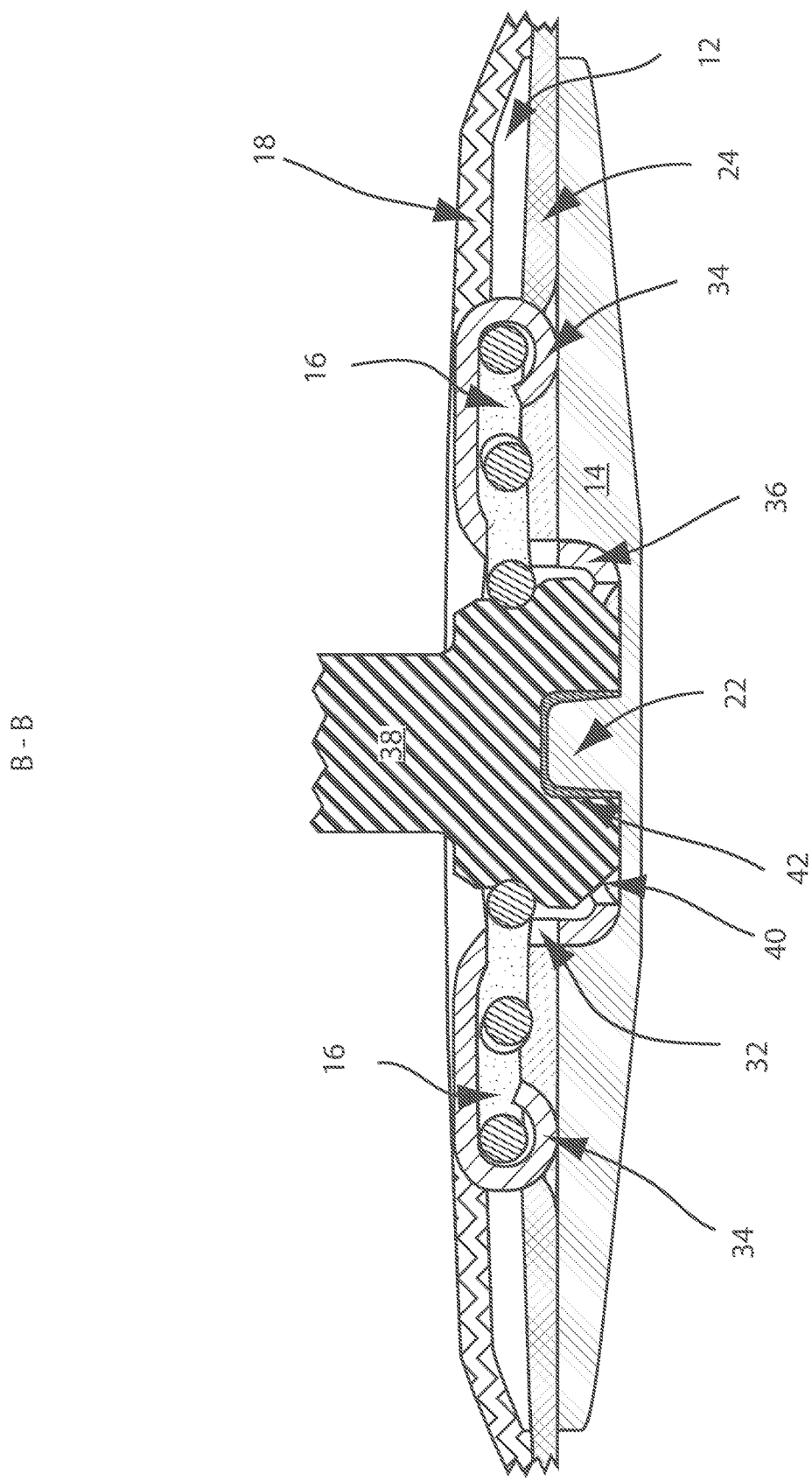
FIG. 3 shows cutaway portion B-B of the integrated snap of FIG. 1 with the material of a garment as well as a male end of a telemetric device inserted in the socket region of the snap.

The base portion 14 of the snap 10 is shown for example in FIGS. 2 and 3. Generally, the base portion 14 of the snap 10 complements the upper cap portion 12. According to the present example of the figures, the base portion 14 includes a recess at, or near the middle of the base portion 14 which corresponds to the recess of the upper cap portion 12. The recess of the base portion 14 is wider than that of the recess of the upper cap portion 12 such that at least a portion of the sides 30 of the upper cap portion 12 fit within the recess of the base portion 14. Having this overlap of the two portions aids in assuring a water tight coupling of the two portions at the socket region 20.

According to the present example, the bottom of the recess of the base portion 14 forms the bottom of the socket region 20. However, as described above, at least a portion of the bottom of the socket region 20 may be formed by the upper cap portion 12.

A guiding stud 22 may be provided at the bottom of the socket region. A guiding stud 22 may be added in order to increase the stability of the connection. In the present example the guiding stud 22 is provided on the bottom surface of the recess of the base portion 14. However, the snap of the present example may not have a guiding pin 22 but be otherwise the same as disclosed herein.

The guiding stud 22 acts to center and stabilize the male end of a telemetric device which has a recess compatible with the geometry and dimensions of the guiding stud. In FIG. 3 a male end of a stud 38 of a telemetric device 50 is shown detachably connected to the snap 10. FIG. 3 shows the cutaway section B-B from FIG. 1.

According to the present example, the guiding stud 22 is an integral portion of the base portion 14. The base portion 14 can be made of a non-conductive material such as a plastic or rubber based material. The guiding stud can be rigid or it may have some, preferably a slight, degree of flexibility. According to certain examples, the guiding stud 22 can be a separate piece which is attached or affixed to the bottom of the socket region. For example, the guiding stud 22 can be a stud or screw which is attached to the bottom of a recess in a base portion during manufacturing. Similarly, if the bottom of the socket region is formed partially or entirely by the upper cap portion 12, the guiding stud may be an integral part, or an additional piece added to the upper cap portion 12. Still yet, the guiding stud may be an integral part, or an additional piece added to a base plate or mat which covers and/or forms the bottom of the socket region. Such a base plate or mat may be, for example a sticker or a piece with an adhesive which is added to the base portion 14 and/or the upper cap portion 12 at the bottom of the socket region 20.

According to certain examples of the present invention the guiding stud 22 can take the geometry of a standard cylinder. Additionally, it can be advantageous for the guiding stud 22 to have a conical geometry, for example as shown in FIG. 3. By having a conical geometry it allows for a stud 38 to have a slightly off alignment when entering the socket region and then aids in the centering and alignment of the stud 38 in to the detachably secured position as shown in FIG. 3.

According to the present examples, the thickest portion of the snap 10 is between the top portion 13 of the upper cap portion 12 and the bottom of the base portion 14 directly underneath the socket region 20. In order to produce a snap which has the least adverse effect on the garment which it is being integrated within, and therefore on the user wearing the garment, it is advantageous to keep this maximum thickness as small as possible. Currently, the standard snap thickness in the industry is around or above 4 mm. With the design of the present snap 10, the maximum thickness of the snap between the top 13 of the upper cap portion 12 and the bottom of the base portion 14 can be between about or even less than 1 to 3 mm or, for example between 1.5 to 2.5 mm. According to certain examples, utilizing the present design can reduce the overall size of the snap portion within a garment by 50-70% or more. This reduction in size is almost solely responsible for the success of integrating heart rate monitors in to garments.

As the snap 10 is, or is to be integrated within a material 18, the overall thickness of the snap 10 can gradually be reduced and/or tapered towards the outer edges, as is seen in the figures. The flange 26 of the upper cap portion 12 is depressed in order to reduce the overall thickness of the snap 10 as well as to allow for better integration with a material layer 18 of a garment. Similarly, as can be seen for example in FIG. 2, the outer portions of the base portion 14 are tapered such that the thickness of the base portion 14 and the snap 10 as a whole is reduced at the edges. FIG. 2 shows an example in which the base portion 14 extends past the edge of the flange 26 of the upper base portion 12. This extension can help in a more seamless integration of the snap 10 within a garment. However, as shown for example in FIG. 3, the base portion 14 may have a radius substantially equal to, or even less than, that of the upper cap portion 12.

As discussed with regards to the embodiments and examples herein, both the upper cap portion 12 and the base portion 14 are generally circular in shape. However, one of ordinary skill in the art will recognize that the geometry of one or both of the upper cap portion 12 and the base portion 14 can be freely selected without departing from the scope of the present invention.

While it is advantageous to minimize the maximum thickness of the snap 10, at the same time it is advantageous to maximize the depth of the socket region of the snap 10 within the overall maximum thickness of the snap 10. According to examples of the present invention the depth of the socket region of the snap between the top 13 of the upper cap portion 12 and the bottom of the socket region is between 1 to 2.5 mm, preferably between 1.5 to 2.5 mm. Similarly, according to examples of the present invention, the depth of the socket region of the snap is between 80 to 98%, preferably between 85 to 97%, still more preferably between 90 to 95% of the maximum thickness of the snap 10.

Within the socket region 20 of the snap 10, according to the present examples and embodiments, it is advantageous for the height of the guiding stud to be at least 0.9 mm from the base of the socket region 20. However, according to certain embodiments and examples, it is advantageous for the height of the guiding stud to be between 0.5 mm to 2 mm, preferably between 0.8 mm to 1.5 mm. Similarly, according to examples of the present invention, the height of the guiding stud is between 20 to 80%, preferably between 30-50% of the depth of the socket region 20.

Additionally, the conductive wire spring 16 can be one of the bulkiest items within the snap. When the conductive wire spring 16 is at least partially housed within a gap created between the upper cap portion 12 and the base portion 14 around the side walls 30 of the socket region 20, it is advantageous to minimize the gap. According to certain embodiments and examples, it is advantageous for the maximum height of the gap to be between 0.5 to 2 mm, preferably between 0.5 to 1 mm.

Although the upper cap portion 12 and base portion 14 are described herein as being separate portions, they may be a single integral piece. However, for manufacturing purposes it is typically advantageous for the upper cap portion 12 and base portion 14 to be separate pieces. According to an example of the present invention, the upper cap portion 12 is a conductive material, e.g. a metal such as stainless steel, and the base portion 14 is a non-conductive material, e.g. a plastic or polymer based material. Similarly, the upper cap portion 12 can be made partially or wholly of a non-conductive material and/or the base portion 14 can be made partially or wholly of a conductive material. As such, it is significantly easier to manufacture the two pieces separately.

When separate pieces, the upper cap portion 12 and the base portion 14 can be coupled in a variety of non-exclusive ways. As discussed above, if the base portion 14 has a recess which corresponds to the recess of the upper cap portion 12, then the upper cap portion 12 and the base portion 14 can be coupled within the recess of the socket region by a mechanical and/or a chemical/adhesive means. Additionally, as shown for example in FIG. 2, the flange 26 of the upper cap portion 12 may comprise one or more openings through which the upper cap portion 12 can be coupled to the base portion 14 by a mechanical means. In the present example the mechanical means is a polymer rivet. However, any number of mechanical means can be used such as, for example, metal or chemical rivets, screws, studs, clips, etc. The mechanical means of connection may be present at, or towards the outer edges of the shorter of the upper cap portion 12 and/or the base portion 14. One of ordinary skill in the art will recognize countless means of attaching the two pieces which do not depart from the scope of the present invention.

A further example of a mechanical connection means 28 is that the base portion 14 comprises a plurality of integral extensions 28 which align with the openings in the upper cap portion 12, and optionally with openings in any electrode and/or other material between the upper cap portion 12 and the base portion 14. The extensions 28 will pass through the openings in the flange 26 and then heat, for example in the form of an ultrasonic or laser application, essentially melts the top portion of the extension such that it forms the cap seen in FIG. 2.

In order for a garment to provide the necessary data to a telemetric transmitter, the garment should be provided with at least one, and typically at least two electrodes 24. Several methods for attaching and integrating an electrode 24 with a material 18 are known, for example as presented in U.S. application Ser. No. 11/808,391 filed Jun. 8, 2007 and published as US 2007/0285868 which has been incorporated by reference in its entirety. Additionally, the electrode 24 should make an electrical connection with a stud 38 of a telemetric transmitter through the snap 10.

As such, as can be seen for example in FIG. 2, the material 18 as shown in FIG. 1 has been removed and it is possible to see that the electrode 24, which is at least partially affixed and/or integrated within the material 18, is sandwiched between the flange 26 of the upper portion 12 and the base portion 14. For a snap which it to be integrated within a garment a gap is left between the flange 26 of the upper cap portion 12 and the outer portion of the base portion 14. According to the present examples, the gap should be equal to, or substantially equal to the thickness, or compressible thickness of an electrode which is to be connected with the snap 10 and or directly to a stud 38 detachably coupled to the snap 10. Within the gap, within another region of the snap or as a portion of either the upper cap portion 12 or the base portion 14, there can be a connector and/or connection region in which an electrode can be electrically connected to the snap or a portion thereof. For example, there can be a conductive region of the upper cap portion 12 which is in electrical contact with both an exposed portion of an electrode 24 as well as the conductive wire spring 16. Such a region can be mechanically or chemically/adhesively, connected to the electrode or the electrode may be frictionally fit against such a conductive or contact region.

According to an embodiment of the present invention a snap is manufactured and subsequently integrated within a garment. In such embodiments the snap may be manufactured in one or more pieces which may or may not correspond to the discrete portions described herein. According to another embodiment, the snap is manufactured in a plurality of pieces and is manufactured along with and integral with a garment or heart rate monitor belt.

As described herein, a garment can be any article which is wearable by a human or animal. Examples of garments which are particularly well suited for use with and incorporation with the present example are tops, shirts, sports bras, bras, undergarments, workout apparel, compression sports t-shirts, shorts, bands and belts. With regards to the remainder of the description, heart rate monitor belts and other specialty articles which one of ordinary skill in the art will recognize can implement the description of the present invention and be worn by a human or animal will be encapsulated in the term garment for simplicity. Furthermore, the garments discussed herein may be made of any suitable material including fabrics, cloths, and other such materials of natural or synthetic origin.

A benefit to the present snap is the flush integration of a snap in to a garment such that a garment having a snap in accordance with aspects of the present invention has minimal if any drawback compared to a garment not having a snap, when no measurement is to be taken by the garment.

Examples of heart rate monitor belts using elastomere or rubber electrodes can be found, for example, in WO 2005/032366. Furthermore, examples of textile electrodes can be found, for example, in WO 2002/071935. In addition to monitoring heart rate, the embodiments and examples herein may also be used for EMG monitoring or measurement. Examples of such measurement devices can be found, for example, in WO 2004/002311 and WO 2005/032365. All of the above mentioned references are herein incorporated by reference in their entirety.

According to certain embodiments wherein the snap is an integral portion of a garment and/or the manufacture of the garment, an electrode 24 can be sandwiched between at least the flange 26 of the upper cap portion 12 and at least a portion of the base 14. Additionally, at least one material layer 18 can be disposed on a top portion of the electrode 24 and may, or may not, extend to cover a portion of the flange 26 or even the top portion 13 of the upper cap portion 12. Furthermore, one or more additional material layers 18 may be disposed on at least a portion of a bottom side of the electrode 24 and/or the bottom portion of the base portion 14 in order to more wholly integrate the snap in to the garment.

Figure 5:
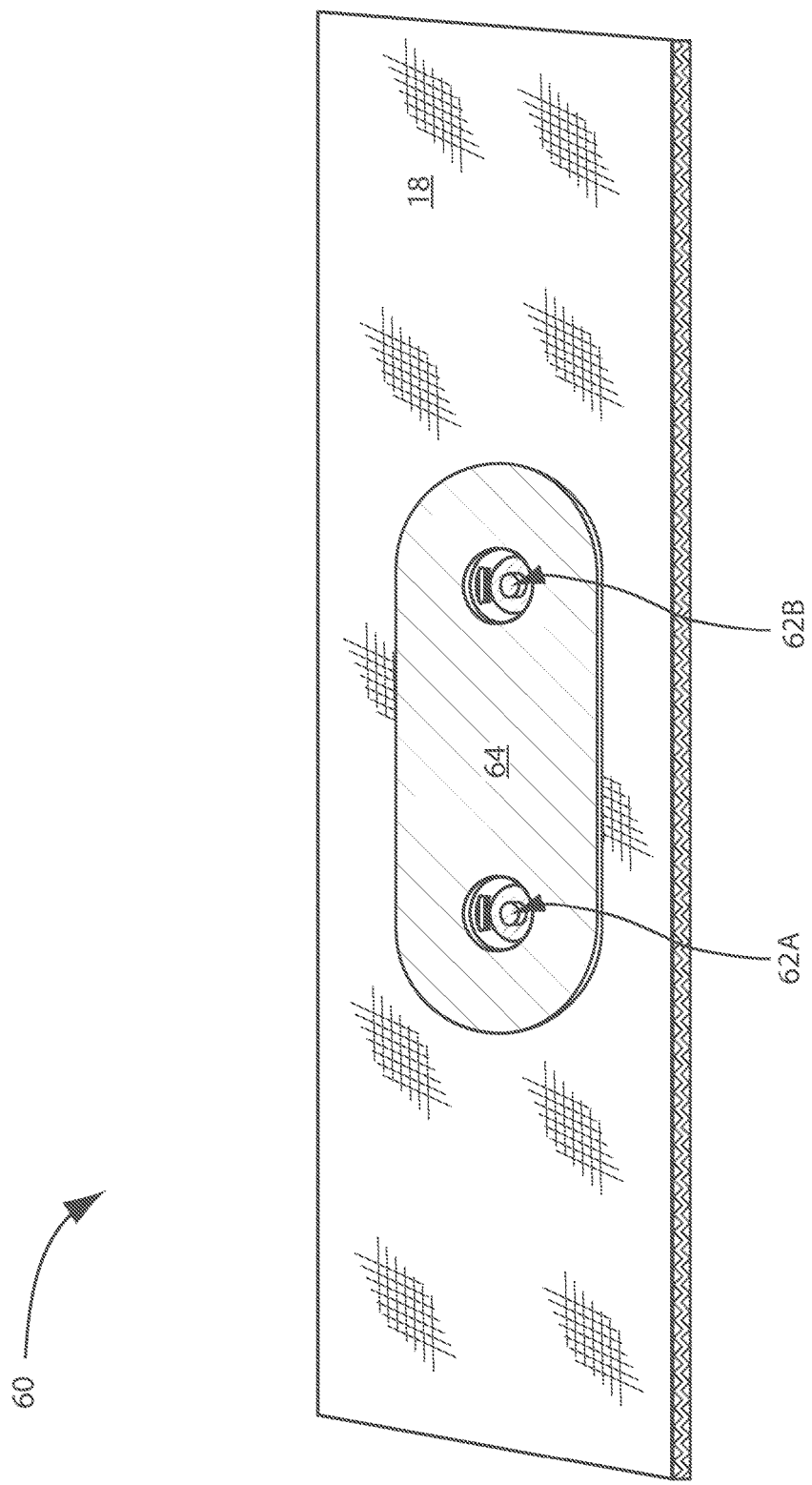
FIG. 5 shows an example of a garment or heart rate monitor belt having two snaps in accordance with an embodiment of the present invention.

FIG. 5 shows an example of a garment 60 which has a top material layer 18 and two electrodes (not shown) which can be coupled to the back of material layer 18 or to another subsequent material layer. Each electrode is connected to a snap, 62A and 62B. Each of snaps 62A and 62B are in accordance with the snaps described herein. In a typical arrangement, the electrode attached to each snap would extend in a direction away from the other snap. As such, there will be an area between the two snaps which may or may not include an electrode or similar material.

Figure 6:
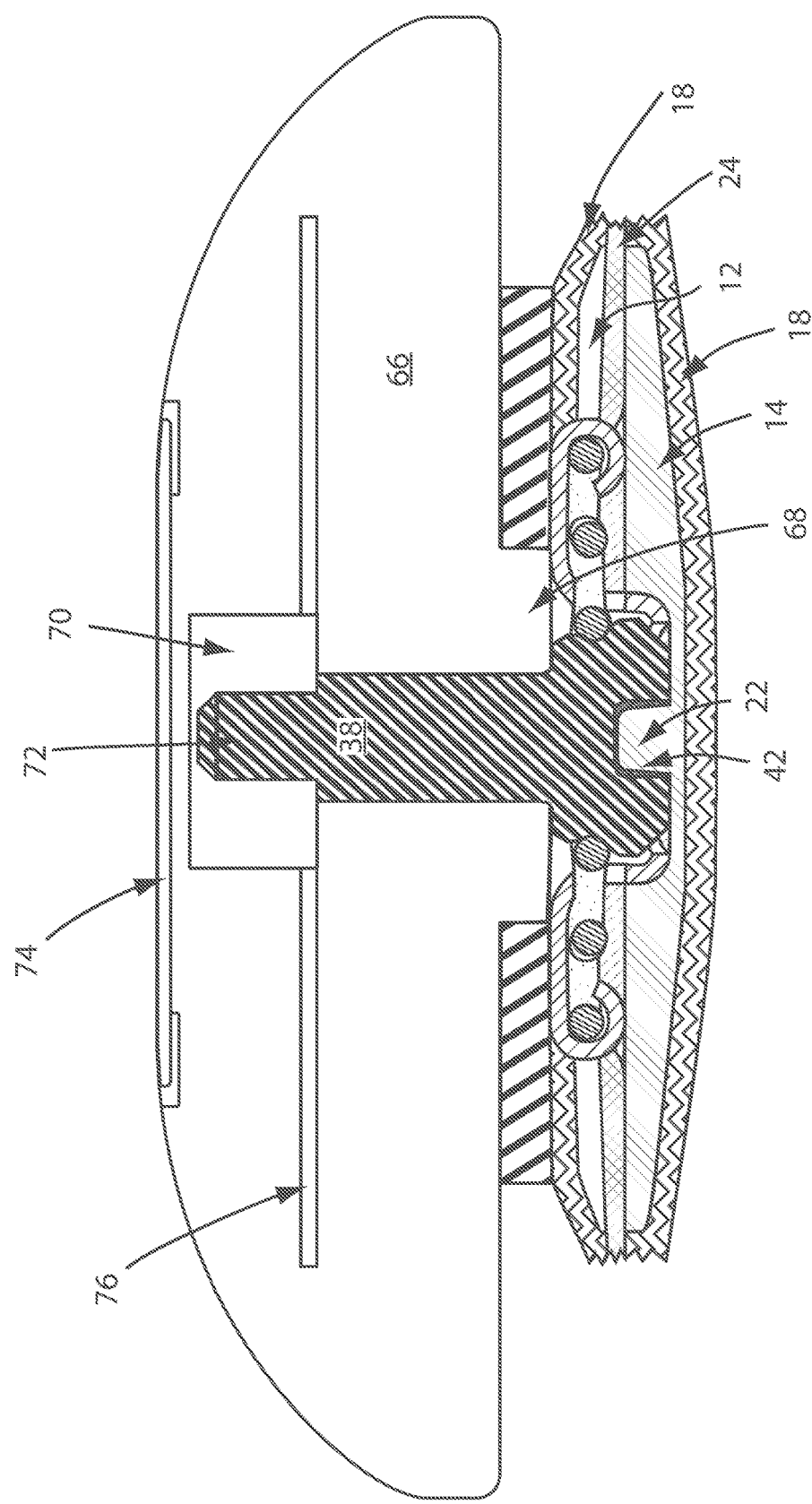
FIG. 6 shows a cutaway of a telemetric transceiver having a stud and male end in accordance with an embodiment of the present invention inserted within the socket region of a snap in accordance with the present invention.

A non-conductive, preferably water-proof material 64 can be added on top of at least a portion of one or both snaps. As shown in FIG. 6, the covering 64 covers a substantial portion of the top portion 13 of the upper cap portion 12, as well as the entire area of the flange 26 of the upper cap portion 12 of each snap. However, the covering 64 does not extend in to or over the recess or over or within the socket area. Additionally, a covering 64 may cover anything from none or a small portion of the top portion 13 of the upper cap portion 12 to virtually all of the top portion 13 of the upper cap portion 12. Furthermore, the covering extends and covers a portion of the area disposed between the two snaps 62A and 62B.

Figure 4:
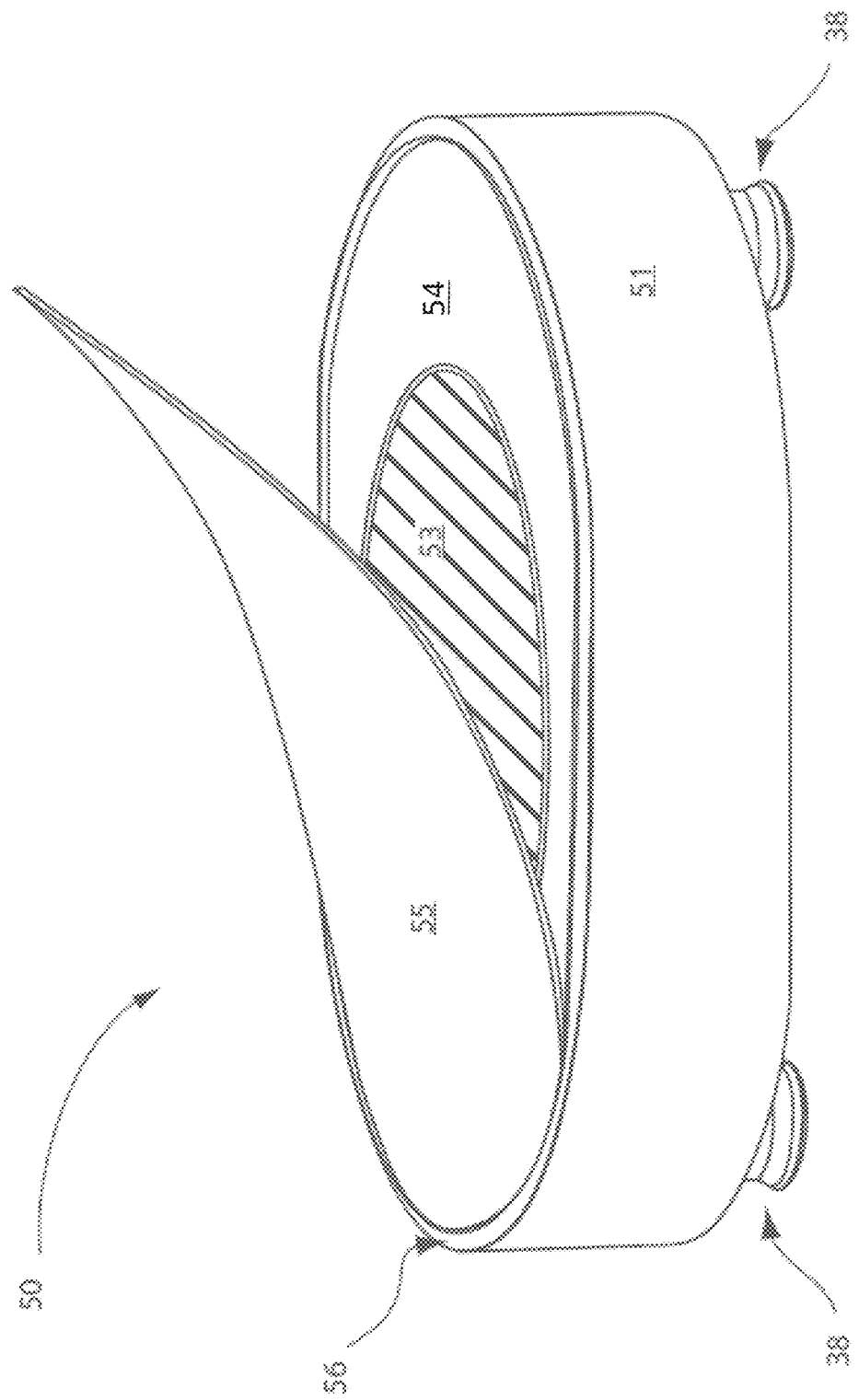
FIG. 4 shows a generic body of a telemetric device comprising male ends in accordance with an embodiment of the present invention.

An example of a telemetric device 50 which is compatible with the garment 60 is shown in FIG. 4. The telemetric device 50 has a body portion 51, an aperture 53 for housing for example a battery, a surface surrounding the aperture 54 surrounded by an outer lip 56 and a cover 55, which can be for example a flexible sticker type cover with or without a graphic or textual display. Additionally, the telemetric device has two studs 38 having an exposed male end for being detachably coupled to the snaps 62A and 62B of garment 60.

As referenced above, it is advantageous for the side walls 30 of the socket region 20 to correspond with the geometry of the male end of the stud 38 of a telemetric device. As can be seen, for example in FIG. 3, the bottom portion of the recess of the upper cap portion 12 is slightly bent/chamfered inwards towards the center of the socket region. Similarly, the head of the stud 38 has corresponding chamfers 40. The chamfers 40 of the stud 38 head allow for easier guiding of the stud 38 in to the socket region of the snap 10.

FIG. 8 shows an example of a stud and electrode assembly in accordance with the present invention. An stud an electrode assembly is useful for the simple integration of the stud and electrode in to a heart rate monitor belt. The stud and electrode assembly comprises an electrode 24, and an integrated snap 10 having an upper cap portion 12, a conductive wire spring 16 in electrical connection with the electrode 24 and a base 14. The conductive wire spring 16 can be held within the snap by, for example, one or more lips 34 formed from corresponding notches 35 in the flange 26 of the upper cap portion 12.

The snap 10 can be arranged at any point and having any orientation with respect to the electrode 24. Additionally, the electrode 24 may take the shape of something other than a strip, as shown in the present example. However, it can be advantageous to integrate the snap 10 at or towards one end of a strip like electrode 24 as shown in FIG. 8.

According to the present example, the snap 10 is arranged near a terminal end of the electrode 24. The wire spring 16 is held within the snap 10 by three lips 34. The three lips 34, and consequently the three corresponding notches 35 are arranged in such a way that no notch opens towards the length of the strip electrode 24. This adds a degree of rigidity and support to the assembly.

Additionally, the openings 32 in the side of the socket region 20 of the snap 10 are arranged to be parallel with the length of the electrode 24. In other words, the openings 32 are arranged to be parallel with the sides of the electrode 24 as seen in FIG. 8. When two snap and electrode assemblies, for example two of the assemblies shown in FIG. 8, are integrated within a heart rate monitor belt, the snap 10 ends of the electrodes 24 will typically be arranged close to each other and the remaining tail portions of the electrodes will extend in opposite directions. When an electronic device is snapped in to the pair of snaps, the arrangement will provide stability in the direction of the arrangement, e.g. taking the orientation of FIG. 8, in the horizontal direction (along the length of the electrode). Thus, with the orientation of the openings 32 and the wire spring 16 as shown in the figure, the wire springs are capable of providing stability in the opposite direction, e.g. taking the orientation of FIG. 8, in the vertical direction (opposite the length of the electrode). Therefore, maximum stability can be obtained.

According to certain embodiments, when assembling the snap and electrode assembly an upper cap portion 12 can be affixed to an electrode 24 by means of, for example, a conductive tape 29. The conductive tape 29 can be seen in FIG. 8 where the notches have been formed in the flange 26. An opening corresponding to the socket region can be performed in the electrode. The conductive tape 29, e.g. a ring of conductive tape 29, can be placed on a first surface of the electrode and then the upper cap portion can be placed thereon. The conductive tape 29 can be a double sided conductive tape, for example having carbon fiber particles and copper plating.

The flange 26 of the upper cap portion 12 may have one or more openings preformed therein. Similarly, the electrode 24 may have one or more opening preformed therein which correspond to openings in the flange 26 or are otherwise for allowing one or more extensions from the base portion to pass there through. Additionally, one or more openings may be formed through the flange of the upper cap portion 12 and/or electrode 24. The base portion 14 is then affixed to the assembly by extensions 28 which pass through the openings in the electrode and flange 26. The extensions 28 are then deformed, for example by means of an ultrasonic, laser or other heating means, in order to form caps and effectively sandwich the electrode between the upper cap portion 12 and the base portion 14.

The snap 10 of the snap and electrode assembly may be in accordance with any of the examples and embodiments of snaps described herein.

FIG. 4 shows a telemetric device 50 having two exposed male head portions of a studs 38. Typically, connection studs for telemetric devices have been molded within a casing of the telemetric device or otherwise integrated during manufacturing in a similar process. However, several problems arise with such manufacturing techniques when the devices are put under extreme conditions or exposed to liquid or vapor. Therefore, there is described herein a novel stud 38 for a telemetric device which is partially threaded and can be screwed in to an opening in a male connection end of a telemetric device. By coating at least a portion of the threads with an adhesive prior to screwing in to place the stud 38 can be securely fastened within the opening and insure a completely water-tight seal between the stud 38 and telemetric device which is far superior to any seal which can be made using a molding technique.

Figure 7C:
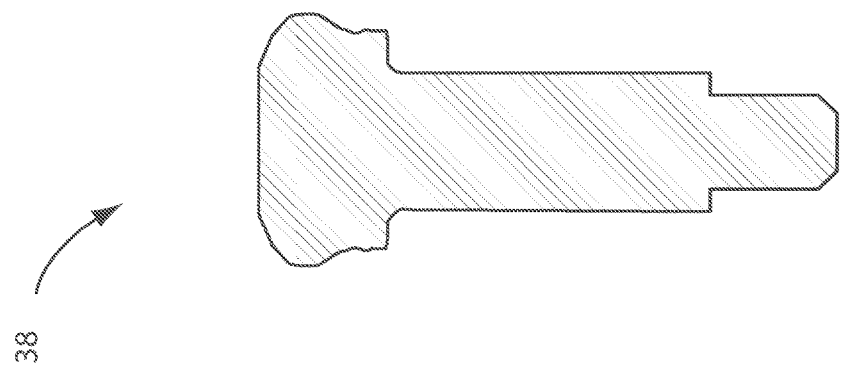
FIG. 7C shows an alternative example cutaway portion of the stud of FIG. 7A without a cavity.
Figure 7B:
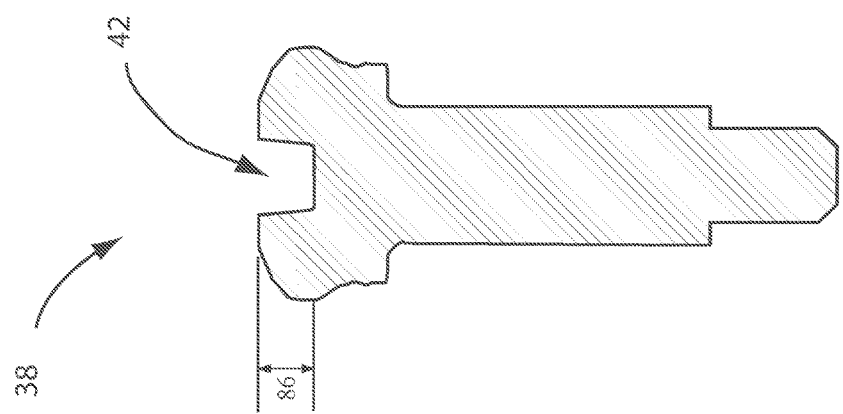
FIG. 7B shows a first example cutaway portion of the stud of FIG. 7A with a cavity.
Figure 7A:
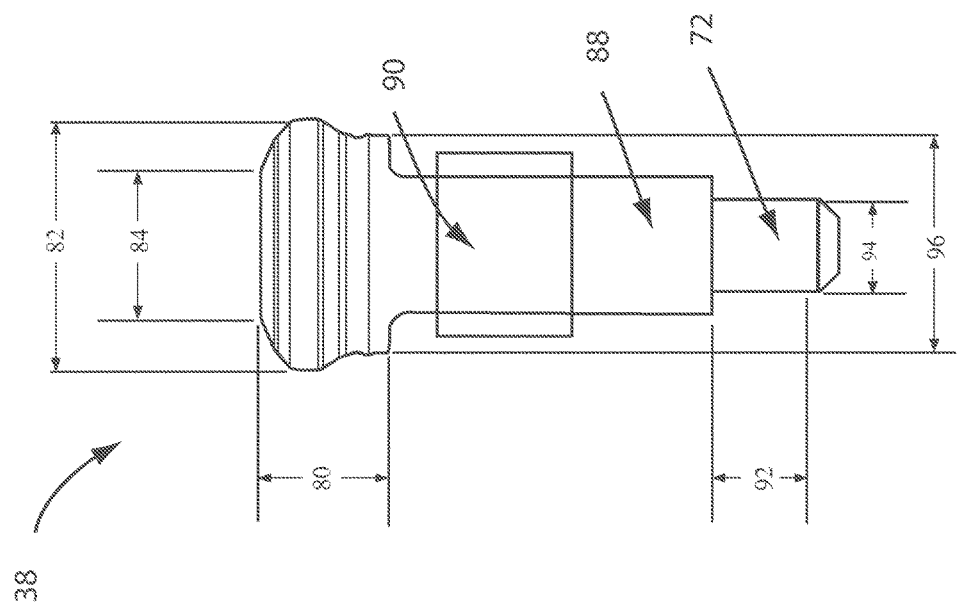
FIG. 7A shows a stud for use in an electronic device in accordance with an embodiment of the present invention.

FIG. 7A shows an example of a stud in accordance with certain embodiments of the present invention. FIG. 7B shows a cutaway section of the stud of 7A. The stud 38 generally comprises or consists of three sections, a male head portion, a mid-portion and an end portion.

At least a portion of the male head portion is capable of fitting within a socket region of a snap. According to preferred embodiments of the present invention, the male head portion of the stud 38 is configured to fit within a socket region 20 of a snap 10 as described above. As such, at least a portion of the male head portion is disposed outside of the housing 51 of an electronic device. According to certain examples the entire head portion is located outside of the housing 51. Furthermore, according to certain examples, only the head portion is located outside of the housing 51.

In terms of the present disclosure, the male head portion has a terminal end which is the terminal end of the stud 38. The male head portion extends between said terminal end and a second end which separates the male head portion from a mid-portion. The length of the male head portion of the stud 80 is the length between the terminal end and the second end.

According to certain examples, the male head portion comprises a chamfered 40 terminal end which is chamfered from a maximum diameter 82 of the male head portion near the terminal end. The chamfer is added to guide a wire spring snap open, for example to guide the conductive wire springs 16 in the socket region 20 of the snap 10 open as the male head portion is inserted in to the snap. If the chamfers are too small then they are not efficiently capable of guising the male head portion of the stud 38 in to a snap. The amount of chamfer is the difference between the maximum diameter 82 of the male head portion and the diameter 84 at the terminal end of the stud.

Additionally, beyond the maximum diameter 82 of the male head portion, towards the mid-portion, is a concave arced recess. The concave arced recess can be seen, for example, in FIGS. 7A, 7B, 7C and 3. The concave arched recess is for making a stable connection with a conductive wire spring 16 of a snap 10. According to the present examples, the concave arched recess is slightly set back from the maximum diameter 82 of the male head portion. The region with the maximum diameter 82 can be flat or it may be at a point or apex of a curve. As shown, for example in FIG. 3, the male head portion may include a chamfer between the maximum diameter 82 of the male head portion and the beginning of the concave arched recess. Such a chamfer can be implemented to keep the male head portion of the stud in place until a critical pulling force is reached. The curvature of the concave arched recess can be selected to complement a desired or standard conductive wire spring 16 diameter.

Beyond the concave arched recess, towards the mid portion, is the second end of the male head portion. The second end may be an imaginary break between the male head portion and the mid-portion. However, according to certain examples, the second end may have a diameter 96 slightly larger than the end of the concave arched recess, and/or a shim, which can act as a stopper during the screwing process of inserting the stud 38 in to an opening of an electronic device. While in most examples the diameter 96 of the shim and/or second end of the male head portion is less than or equal to the maximum diameter 82 of the male head portion, the diameter 96 of the shim and/or second end of the male head portion may be larger than the maximum diameter 82 of the male head portion.

The end portion 72 of the stud is opposite the male head portion. The end portion has a terminal end which is the second terminal end of the stud, opposite the terminal end of the male head portion of the stud 38. The end portion extends a distance from the second terminal end of the stud to the mid-portion of the stud which is the length 92 of the end portion 72 of the stud 38. The division between the mid-portion of the stud and the end portion may be an imaginary break. However, the division between the mid-portion of the stud and the end portion may be a change in diameter and/or the break between the threaded portion and non-threaded portion at the opposite end of the stud from the male head portion.

According to certain examples, the end portion 72 of the stud is characterized in that it is non-threaded. Additionally, the terminal end of the end portion 72 can be chamfered inwards from the diameter 94 of the end portion 72. The end portion 72 of the stud is for making an electromechanical connection between the stud 38 and a component of the electrical device.

In between the male head portion and the end portion 72 is the mid-portion 88. According to certain examples, the mid-portion is characterized in that it is at least partially threaded. Additionally, according to certain examples the entire mid-portion 88 of the stud is threaded. The threads of the mid-portion 88 are a means of securing the stud 38 in an opening of an electronics device. An example of the threading for the mid-portion is Remform F 2.5 mm.

According to certain examples, the mid-portion 88 of the stud 38 has a constant diameter. Additionally, according to certain examples, the diameter of the mid-portion 88 is less than the diameter 96 at the second end of the male head portion. Furthermore, according to certain examples, the diameter of the mid-portion 88 is greater than the diameter 94 of the end portion 72 of the stud 38.

According to certain embodiments of the present invention, the male head portion has a centered cavity 42 which is open at the terminal end of the male head portion. An example of such a cavity 42 is shown in the cutaway FIG. 7b. The cavity 42 is for fitting over a guiding stud 22 of a snap 10 in accordance with the disclosure above. The presence of a guiding stud 22 in a snap 10 and a corresponding cavity 42 in a male head portion of a stud 38 allows for enhanced stability of the connection between the stud 38 and the snap 10 allowing for a significantly more compact snap design. While according to preferred embodiments the cavity 42 is centered on the terminal end of the male head portion, the cavity 42 may be off center according to other embodiments.

Additionally, the cavity can be utilized as a recess for a Torx or other tool during the screwing process during manufacturing when the stud 38 is inserted in to an opening of an electronics device. As such, the cavity can have a variety of dimensions and geometries including, for example, a cylindrical cavity, a conical cavity, a TORX PLUS, e.g. 10IP, 8IP or 6IP, geometry, cubic cavity and/or similar geometry or combination of thereof. The cavity may correspond directly to a guiding stud 22 of a snap 10 to which the stud 38 is to be inserted. Additionally, the cavity may have a different geometry which is merely compatible with the geometry of the guiding stud 22. For example, the cavity may have a TORX PLUS IP6 geometry which has a diameter of 1.75 mm and the guiding stud may be cylindrical or conical having a maximum diameter of 1.75 mm or slightly less.

According to certain examples, the depth 86 of the cavity 42 should be at least 0.9 mm. According to other examples, the depth can be between 0.5 to 1.5 mm.

FIG. 7c shows an alternative example of a stud in accordance with the present invention in which the stud does not have a cavity 42.

According to one example of a stud in accordance with the present invention, the length 80 of the male portion of the head is 2.1 mm, the maximum width 82 of the male portion of the head is 4.1 mm, the diameter 84 of the terminal end of the male head portion is 3 mm, the depth 86 of the cavity is 1.5 mm, the length of the mid-portion is 5 mm, the length 92 of the end portion is 2 mm, the diameter 96 of the second end of the male head portion is 3.6 mm, the threading of the mid-portion is Remform F 2.5 mm and the diameter 94 of the end portion is 1.5 mm.

More generally, the length 80 of the male portion of the head can be between 1 to 3 mm, the maximum width 82 of the male portion of the head can be between 3.9 to 4.3 mm, the diameter 84 of the terminal end of the male head portion can be between 2.8 to 3.6 mm, the depth 86 of the cavity can be between 0.8 to 1.5 mm, the length of the mid-portion can be between 3 to 5 mm, the length 92 of the end portion can be between 0 to 3 mm, the diameter 96 of the second end of the male head portion can be between 3 to 4 mm and the diameter 94 of the end portion can be between 1 to 2 mm.

Additionally, there is disclosed herein an electronic device 50 having a housing 51 and at least one male connection portion as shown for example in FIG. 6. The male connection portion(s) of the electronic device 50 are for detachably connecting the electronic device 50 to a female snap 10. The male connection portion(s) of the electronic device 50 comprise a stud 38 as discussed above.

As shown, for example in FIG. 6, the entire male head portion of the stud 38 according to the present example is outside the housing 51 of the electronics device 50. In accordance with preferred embodiments, the stud is made of an electrically conductive material. Additionally, one purpose of the stud is to facilitate an electrical connection between a portion of a snap 10 and an electronic component 76 of an electronics device 50. However, one of ordinary skill in the art will recognize embodiments of a stud 38 which is only partially made of a conductive material which can facilitate the electrical connection disclosed herein and as such would not depart from the scope of the present invention.

As described above, the stud 38 is threaded and is screwed in to an opening of the housing 51 of an electronic device during manufacturing. During or prior to the stud 38 being inserted and/or screwed in, at least a portion of the threads of the mid-portion of the screw are covered in and/or in contact with an adhesive. An example of an adhesive is Spedcaps Orange. The adhesive not only secures the stud 38 within the housing of the electronics device but it also helps form a water tight barrier between the environment and the electronic component 76.

During manufacturing, an opening can be formed or manufactured in the housing 51 and/or internal cavity of an electronics device 50. The opening can be threaded or unthreaded. In examples where the opening is unthreaded the material can be such that a threading is formed within the opening while the stud 38 is being screwed and/or inserted in to the opening. Additionally, while the present description describes an opening being preformed within a housing and/or cavity of an electronics device, one of ordinary skill will recognize embodiments in which a stud 38 can partially or wholly create its own opening in a housing and/or cavity of an electronics device, said embodiments which would not otherwise depart from the scope of the present invention.

At or towards the end of the opening in the electronics device 66 is a component in which the end portion of the stud 38 is to be in electromechanical connection. The component may be an electronics component 76 of the electronics device 66. Additionally, for example in order to account for variations in the manufacturing process, at the end or towards the end of the opening may be a spring contact 70 which the stud 38 is electromechanically connected to once screwed/inserted in to the opening. The spring contact 70 can then be electrically connected to an electronic component 76 such as a printed circuit board. The electric component 76 can be accessible by a cover 74 on top of the electronics device 66.

Additionally, the housing 51 of the electronics device 50 may include a protrusion 68 at the male connection portion. The male head portion of the stud 38 may be partially or entirely outside of the housing and protrusion 68 of the electronics device 50. The protrusion 68 can extend from the second end of the male head portion of the stud, e.g. the shim, at least partially along the mid-portion of the stud 38. The protrusion 68 may extend, for example, between 0 to 2 mm from the base of the electronics device. Additionally, the protrusion 68 may have a diameter greater than the maximum diameter 82 of the male head portion of the stud.

According to an example of a system having an electronics device 50 and at least one snap 10 in accordance with the present description, the snap 10 can have a sealer 64, for example as shown in FIG. 5. The sealer can be set back from the socket region 20 by a predetermined amount. Similarly, the protrusion 68 of the male connection portion can be designed to fit snugly within the gap left by the sealer 64, as shown for example in FIG. 6. As such, the outer diameter of the protrusion 68 is substantially equal to, or slightly smaller than, the opening in the sealer 64. Similarly, the length of the protrusion 68 can be substantially equal to or slightly more or less than the thickness of the sealer 64.

Described herein, the electronic device 50 can be a telemetric transmitter and/or telemetric transceiver. Examples of telemetric transmitters and transceivers modules used with heart rate monitor belts to transmit information relating to the heart beat of a user to a remote receiver. One of ordinary skill in the art will recognize countless electronic devices and telemetric devices which can be used within the scope of the present invention. Such electronic devices may or may not comprise a display and may or may not be capable of wirelessly transmitting information. Additionally, they may be capable of sending a wide variety of data not limited to heart rate to a remote receiver.

Furthermore, disclosed herein is a system comprising one or more snaps 10 as described herein in combination with an electronic device having one or more studs 38 as described herein. Such a system can take the form of, for example, a heart rate monitor belt and a telemetric device for transmitting heart rate data from the heart rate monitor belt.

As discussed above, the snaps as described herein are particularly well suited for integration in to garments. However, the spacing between the snaps when integrated in to a garment should be within a small tolerance of the spacing of the telemetric device. While current manufacturers of heart rate monitor belts have the equipment and experience to achieve this degree of installation, the garment industry en mass does not. Therefore, there is provided herein an electrode assembly 120 as shown in FIGS. 9-11.

FIG. 9 shows an exploded view of an example electrode assembly 120. The electrode assembly can be delivered to a user in one or more pieces. For example, the electrode assembly may be distributed in a single assembled form, as shown for example in FIG. 11. The electrode assembly may also come in one or more pieces, for example with two electrode 24 and upper cap portion 12 sub assemblies as shown in FIG. 8 and a linking member 110 as shown in FIG. 10. Furthermore, other sub assemblies can be fashioned from the parts disclosed herein.

FIG. 9 shows the exemplary portions of an electrode assembly 120 including a first electrode 24 having an upper cap portion 12, a second electrode 24 having an upper cap portion 12, a first base portion 14 of a snap, a second base portion of a snap 14 and a non-stretchable material portion 102. Typically the two base portions 14 and the non-stretchable material portion 102 are preformed in a single linking member 110 as shown in FIG. 10. The upper cap portion 12, electrode 24 and base portion 14 can be according to any of the examples and embodiments described above. Furthermore, the electrodes 24 can be electrode strips, of varying lengths and dimensions, as shown in FIGS. 8, 9 and 11.

Figure 10:
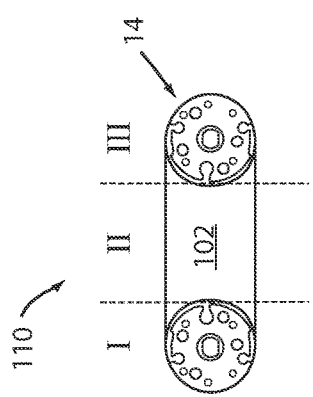
FIG. 10 shows an example of a linking member.
Figure 11:
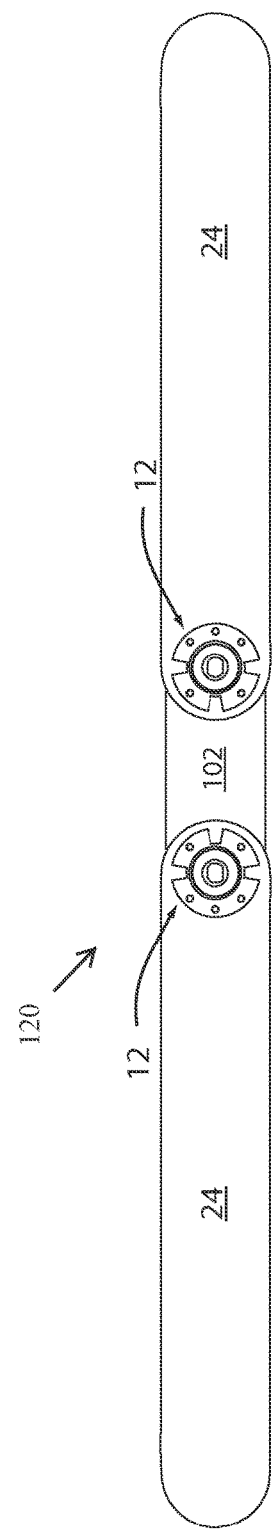
FIG. 11 shows an electrode assembly 120 in an assembled embodiment.

FIG. 10 shows an example linking member 110. In one embodiment the base portions 14 are formed of a first material with a rigidity high enough to properly function as the base of a snap, such as a rigid plastic. In order to enhance the wearability of garments having an electrode assembly integrated therein, the rigid base portions are connected by a non-stretchable material portion 102 which has a rigidity less than that of the base portions 14. The non-stretchable material portion 102 should be non-stretchable so that in an undeformed state the spacing between the base portions 14 is unchangeable. However, when a garment is being worn without a telemetric device 50 attached to the snaps then it helps the wearability of the garment for the connecting portion between the snaps to be able to bend.

As is shown in FIG. 10, the linking member 110 has three rigidity sections, I, II and III. Sections I are III are typically the same, but mirrored construction and have the same rigidity. These sections, typically at least mostly the base portion 14, are as described above with regards to base portion 14. According to certain examples, the sections I and II, and/or base portions 14, are essentially rigid. The middle section 102, according to certain examples, is essentially flexible. As such, according to certain examples the first and second base portions have a first rigidity and the non-stretchable material portion has a second rigidity lower than the first rigidity.

According to certain embodiments, the base portions 14 are made separately and then combined with the non-stretchable material portion 102. In some examples, the base portions 14 are made of a first material and the non-stretchable material portions 102 are made of a second material. The base portions 14 may be premade and then heat molded with the second material to form the linking member 110. The base portion 14 may have one or more portions of its perimeter geometry 104a-c which are complemented by one or more portions of the perimeter geometry 106a-c of the non-stretchable material portion 102. These complementary perimeter geometry portions can help with the chemimechanical bonding in the heat molding. These complementary perimeter geometry portions may also be sufficient to provide a mechanical coupling between the base portions 14 and the non-stretchable material portion 102 on their own. Adhesives or other coupling methods may also be employed. Examples of the non-stretchable material are flexible polymers and plastics as well as non-stretchable technical fabrics.

The linking member 110 can an integral member. The linking member 110 can be formed of a single material. When the linking member 110 is formed of a single material, the material forming the base portions and sections I and III should be of a sufficient rigidity to act as the base portion of the snap. In order to make the non-stretchable material portion flexible, or more flexible, regardless of the composition of the linking member 110, the non-stretchable material portion can have structural elements which reduce its rigidity compared to the first and second base portions. Examples of such structural elements are: slits, gaps in the material, valleys in the material, holes in the material and areas with material of less thickness than other areas.

As described above, the electrode assembly 120 can be a kit and at least one of the following pieces may not be coupled to its respective portion: the first electrode, the upper cap portion of the first electrode, the second electrode, the upper cap portion of the second electrode and the linking member. The base portions may also come separate from the linking member, particularly in embodiments where the base portions are merely mechanically coupled to the non-stretchable material portion. As such, first electrode 24 and the second electrode 24 can be coupled or coupleable to their respective first and second base portions 14 of the linking member 102.

Additionally, the upper cap portions 12 can be located, coupled, coupleable and/or affixed to one side of the electrode 24. Where each upper cap portion 12 has a flange 26 then each flange can comprise a plurality of openings for securing the upper cap portion to the respective electrode and base portion. Each electrode can then have a complementary set of openings and each base portion can have a complementary set of extensions for fitting through the openings in the upper cap portions and the respective electrodes for securing the assembly.

FIG. 11 shows an example of an electrode assembly which is a single unit, and wherein the first electrode and the second electrode are coupled to their respective first and second base portions of the linking member. While the electrode assembly is shown in the figures in an embodiment with only two snap portions, electrode assemblies may comprise one or more further snap portions. Similarly, the linking member 110 may have one or more further base portions. An electrode assembly with more than two snap portions may have a single linking member 110 containing all of the base portions. An electrode assembly with more than two snap portions may have multiple linking members 110 with equal or different numbers of base portions. Furthermore, an electrode assembly with more than two snap portions may have a single linking member with the construction similar to that shown in the figure along with additional base portions 14 attached to electrodes 24 and not attached directly to any particular linking member.

Any of the electrode assemblies 120 discussed above can easily be integrated in to a garment. Electrode assemblies can be integrated in to a garment, for example, by being sewn onto or between a layer of material. Other methods of integration including lamination, being actually built in to the garment or having the material wholly or partially manufactured around the assembly are possible.

When integrated in to a garment, at least a portion of both the first and second electrodes can be arranged such that they are capable of being in direct contact with the skin of a user during normal use of the garment, e.g. on the inside of a garment. Additionally, when integrated in to a garment, at least a portion of each of the upper cap portions can be directly accessible on a side of the garment to be worn away from the wearer such that the snaps are accessible when the garment is being worn. An example of which is shown in FIG. 5. Similar to FIG. 5, the garment may further include a sealer 64.

Electrode strips may also have longer conductive path sections. For example, the electrodes 24 can have a first portion which is to be arranged such that it will be against the skin of a wearer and a second portion which is a conductive path portion which is to be isolated from the skin. The electrode 24, or only a portion thereof such as the conductive portion, can be made with a conductive textile material in place of a standard conductive elatomer. These types of constructions can enable longer paths for lower voltage EMG signals.

A garment is essentially anything that can be worn. Examples of such garments are sports shirt, sports bra, technical shirt, underwear, compression garment, heart rate monitor belt, elastic band and athletic pants. The electrode assemblies can be integrated in any portion of the garments. For example, in sports bras the electrode assembly can be located essentially in the middle of the sports bra and can be easily used with a telemetric device for monitoring heart rate information. Another example is in shirts, one electrode assembly can be located near the chest of the garment for monitoring heart rate information and one or more additional electrode assemblies can be located on or near the arms for muscle measurement, e.g. EMG. Similarly, a pair of pants or shorts can have multiple electrode assemblies integrated in areas around muscle groups to be monitored.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

10—snap
12—upper cap portion
13—top portion of the upper cap portion
14—base portion
16—conductive wire spring
18—material
20—socket region
22—guiding pin
24—electrode
26—flange of upper cap portion
28—mechanical connection means
29—conductive tape
30—sides of the socket region
32—opening in side of the socket region
34—lip of the upper cap portion
35—notch in flange
36—chamfered region of the upper cap portion
38—stud
40—chamfered portion of the pin
42—recess of pin
50—telemetric device
51—body portion of the telemetric device
53—aperture of the telemetric device
54—surface surrounding the aperture
55—sticker cover of the telemetric device
56—lip of the telemetric device
60—garment
62A—first snap
62B—second snap
64—sealer
68—protrusion
69—sealing ring
70—spring contact to PCB
72—non-threaded pin end
74—cover
76—printed circuit board
80—length of the male head portion of the pin
82—maximum diameter of the male head portion of the pin
84—width of the chamfered edge of the head of the pin
86—depth of the recess of the head of the pin
88—threaded portion of the pin
90—adhesive
92—length of the non-threaded pin end
94—width of the non-threaded pin end
96—width of contact portion of the head of the pin
102—non-stretchable material portion
104a-c—portions of the perimeter geometry of the base portion 14
106a-6—portions of the perimeter geometry of the non-stretchable material portion 102 which are complementary to the portions of the perimeter geometry 104a-c of the base portion
108—lip of the non-stretchable material portion for receiving an electrode 24
110—linking member
I, II & III—different rigidity zones of the linking member 110
120—electrode assembly

The invention claimed is:
1. An electrode assembly comprising;
a first electrode having an upper cap portion of a first snap on one side,
a second electrode having an upper cap portion of a second snap on one side,
said upper cap portions each having a respective recess forming at least a portion of a side wall of a socket region of each snap for receiving a male end of a telemetric device and comprising an outer flange region which at least partially surrounds the recess,
a linking member having a first base portion of the first snap and a second base portion of the second snap separated by a non-stretchable material portion,
said first and second electrodes being coupleable to the linking member by the respective first and second base portions, wherein
for each electrode, the outer flange region of the upper cap portion is depressed towards said base portion to reduce a thickness of the snap and to integrate said snap in a garment with a top surface of said upper cap portion flush with a material layer of said garment disposed on top of the electrode.

2. The electrode assembly according to claim 1, wherein the upper cap portions further each comprise a conductive wire spring mechanically affixed to the upper cap portion.

3. The electrode assembly according to claim 2, wherein the upper cap portions further each comprise at least one lip which mechanically couples the conductive wire spring to its respective upper cap portion.

4. The electrode assembly according to claim 2, wherein the upper cap portions further each comprise at least one lip which mechanically couples the conductive wire spring to its respective upper cap portion and said at least one lip is a tab cut from the outer flange region of said upper cap portion and is bent towards the recess.

5. The electrode assembly according to claim 1, wherein the non-stretchable material portion is flexible.

6. The electrode assembly according to claim 1, wherein the first and second base portions are rigid.

7. The electrode assembly according to claim 1, wherein the first and second base portions have a first rigidity and wherein the non-stretchable material portion has a second rigidity lower than the first rigidity.

8. The electrode assembly according to claim 1, wherein the first base portion, second base portion and the non-stretchable material portion are made of the same material.

9. The electrode assembly according to claim 1, wherein the first base portion; and second base portion are made of a first material and the non-stretchable material portion is made of a second material having a lower rigidity than that of the first material.

10. The electrode assembly according to claim 1, wherein non-stretchable material portion has structural elements which reduce its rigidity compared to the first and second base portions.

11. The electrode assembly according to claim 10, wherein said structural elements are selected from the group of: slits, gaps in the material, valleys in the material, holes in the material, and areas with material of less thickness than other areas.

12. The electrode assembly according to claim 1, wherein the first base portion, second base portion and the non-stretchable material portion form an integral member.

13. The electrode assembly according to any of the preceding claims, wherein the first base portion and the second base portion are mechanically or chemi-mechanically bonded to the non-stretchable material portion.

14. The electrode assembly according to claim 1, wherein each outer flange region of said upper cap portion comprises a plurality of openings for securing the upper cap portion to the respective electrode and base portion of said linking member, each electrode has a complementary set of openings, and each base portion has a complementary set of extensions for fitting through the openings in the upper cap portions and the respective electrodes for securing the assembly.

15. The electrode assembly according to claim 1, wherein the electrode assembly is a single unit, and wherein the first electrode and the second electrode are coupled to their respective first and second base portions of the linking member.

16. The electrode assembly according to claim 1, wherein the electrode assembly is a kit and at least one of the following pieces is not coupled to its respective portion: the first electrode, the upper cap portion of the first electrode, the second electrode, the upper cap portion of the second electrode and the linking member.

17. A garment having integrated therein an electrode assembly comprising;

a first electrode having an upper cap portion of a first snap on one side,
a second electrode having an upper cap portion of a second snap on one side, and
a linking member having a first base portion of said first snap and a second base portion of said second snap separated by a non-stretchable material portion,
said first and second electrodes being coupleable to the linking member by respective first and second base portions, wherein
for each electrode, said upper cap portions having a recess forming a socket region of the respective snap and comprising an outer flange region which at least partially surrounds the recess, said outer flange region being depressed towards said base portion to reduce a thickness of the snap and to integrate said snap in said garment having a top surface of said upper cap portion flush with a material layer of said garment disposed on top of each electrode.

\* \* \* \* \*

UNITED STATES PATENT AND TRADEMARK OFFICE
CERTIFICATE OF CORRECTION

PATENT NO. : 9,861,291 B2
APPLICATION NO. : 14/144627
DATED : January 9, 2018
INVENTOR(S) : Pernu et al.

Page 1 of 1

It is certified that error appears in the above-identified patent and that said Letters Patent is hereby corrected as shown below:

On the Title Page

Item (72) should read:
(72) Inventors: Kimmo Pernu, Vantaa (FI);
               Tapio Selby, Vantaa (FI);
               Ossi Lehtinen, Vantaa (FI)

Signed and Sealed this
Twelfth Day of February, 2019

Andrei Iancu
*Director of the United States Patent and Trademark Office*